US008403312B2

(12) United States Patent
Zhang et al.

(10) Patent No.: US 8,403,312 B2
(45) Date of Patent: Mar. 26, 2013

(54) ADJUSTABLE FIXTURE

(75) Inventors: Li-Hua Zhang, Shenzhen (CN); Ke Zhou, Shenzhen (CN); Zi-Zhong Zhang, Shenzhen (CN); Zhen-Wei Zhao, Shenzhen (CN)

(73) Assignees: Shenzhen Futaihong Precision Industry Co., Ltd., Shenzhen (CN); FIH (Hong Kong) Limited, Kowloon (HK)

( * ) Notice: Subject to any disclaimer, the term of this patent is extended or adjusted under 35 U.S.C. 154(b) by 865 days.

(21) Appl. No.: 12/542,822

(22) Filed: Aug. 18, 2009

(65) Prior Publication Data

US 2010/0225036 A1 Sep. 9, 2010

(30) Foreign Application Priority Data

Mar. 5, 2009 (CN) .......................... 2009 1 0300700

(51) Int. Cl.

| | |
|---|---|
| ***B23Q 1/25*** | (2006.01) |
| ***B23Q 3/00*** | (2006.01) |
| ***B25B 1/00*** | (2006.01) |
| ***A61B 19/00*** | (2006.01) |
| ***B60B 29/00*** | (2006.01) |
| ***B65G 7/00*** | (2006.01) |
| *H01L 21/687* | (2006.01) |

(52) U.S. Cl. ............ 269/58; 269/16; 606/130; 414/426

(58) Field of Classification Search .................... 269/58, 269/57, 16; 606/130, 104; 414/1, 4, 427, 414/426, 592, 620

See application file for complete search history.

(56) References Cited

U.S. PATENT DOCUMENTS

| | | | | | |
|---|---|---|---|---|---|
| 3,481,494 | A * | 12/1969 | Walischmiller | 414/1 |
| 3,643,935 | A * | 2/1972 | Bell | 269/16 |
| 3,888,362 | A * | 6/1975 | Fletcher et al. | 414/620 |
| 4,482,130 | A * | 11/1984 | Paredes | 254/8 R |
| 4,762,455 | A * | 8/1988 | Coughlan et al. | 414/4 |
| 5,549,499 | A * | 8/1996 | Foskey et al. | 446/268 |
| 5,695,500 | A * | 12/1997 | Taylor et al. | 606/130 |
| 5,704,601 | A * | 1/1998 | Mangelsen et al. | 269/57 |
| 6,676,669 | B2 * | 1/2004 | Charles et al. | 606/130 |
| 6,719,566 | B2 * | 4/2004 | Farenholtz et al. | 434/267 |
| 6,723,106 | B1 * | 4/2004 | Charles et al. | 606/130 |
| 7,250,028 | B2 * | 7/2007 | Julian et al. | 600/229 |
| 7,625,383 | B2 * | 12/2009 | Charles et al. | 606/130 |
| 7,695,481 | B2 * | 4/2010 | Wang et al. | 606/130 |
| 7,892,243 | B2 * | 2/2011 | Stuart | 606/130 |
| 7,987,811 | B2 * | 8/2011 | Zhang et al. | 118/500 |
| 8,061,952 | B1 * | 11/2011 | Scherden | 414/427 |
| 8,182,491 | B2 * | 5/2012 | Selover et al. | 606/104 |
| 2006/0103222 | A1 * | 5/2006 | Caruso et al. | 297/452.15 |
| 2007/0286714 | A1 * | 12/2007 | Frost | 414/592 |
| 2009/0035107 | A1 * | 2/2009 | Duran et al. | 414/426 |
| 2009/0044731 | A1 * | 2/2009 | Crook et al. | 108/50.14 |

FOREIGN PATENT DOCUMENTS

CN 101083146 A 12/2007

* cited by examiner

*Primary Examiner* — Lee D Wilson
*Assistant Examiner* — Alvin Grant
(74) *Attorney, Agent, or Firm* — Altis Law Group, Inc.

(57) ABSTRACT

An adjustable fixture comprises a clamping board used to mount a workpiece thereon, a hollow telescopic sleeve, a latching assembly, a telescopic shaft, and a fastening seat. The clamping board is fastened to the telescopic sleeve. The telescopic sleeve slidably receives the telescopic shaft therein. The latching assembly is mounted on the telescopic shaft and resists an interior wall of the telescopic sleeve to position the telescopic shaft relative to the telescopic sleeve. The telescopic shaft is rotatably mounted on the fastening seat.

19 Claims, 6 Drawing Sheets

ADJUSTABLE FIXTURE

BACKGROUND

1. Technical Field

The present disclosure relates to fixtures and, particularly, to an adjustable fixture used for painting a workpiece.

2. Description of Related Art

With the development of technology, a user can have high expectations regarding appearance of portable electronic devices, e.g., mobile phones and notebooks. Painting is an effective method to achieve a great appearance.

Usually, a portable electronic device is fixed on a fixture, and then spray painted. However, the typical fixture cannot be adjusted according to need, thus paint coats may not be applied evenly on the portable electronic device, influencing the appearance of the portable electronic device.

Therefore, there is room for improvement within the art.

BRIEF DESCRIPTION OF THE DRAWINGS

Many aspects of an adjustable fixture can be better understood with reference to the following drawings. These drawings are not necessarily drawn to scale, the emphasis instead being placed upon clearly illustrating the principles of the present adjustable fixture. Moreover, in the drawings like reference numerals designate corresponding sections throughout the several views.

DETAILED DESCRIPTION

The present adjustable fixture is suitable for fixing a workpiece, e.g., a mobile phone or a notebook mounted thereon for painting. The workpiece can be neatly adjusted in three dimensions.

Figure 1:
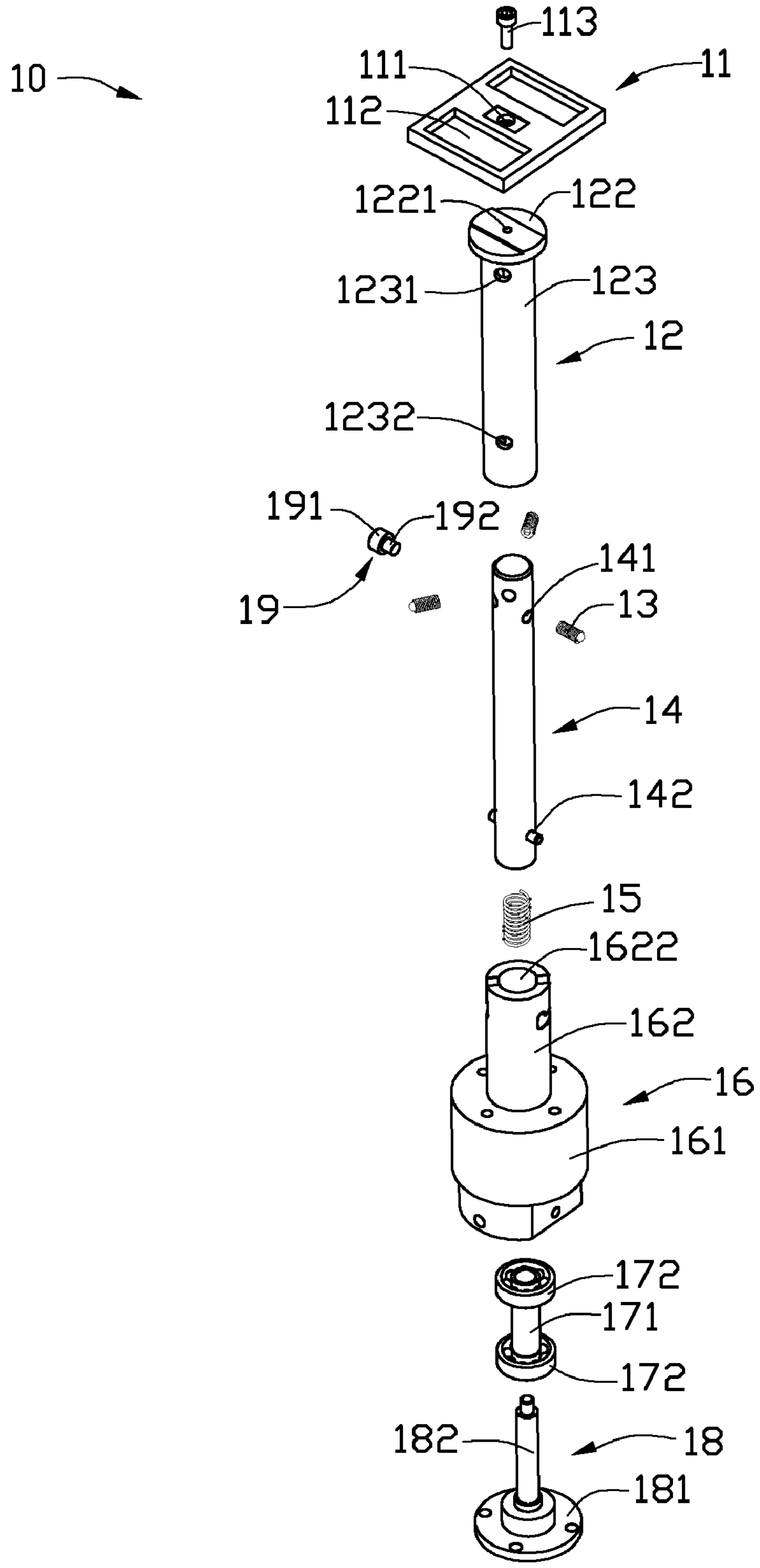
FIG. 1 is an isometric, exploded view of an adjustable fixture, in accordance with an exemplary embodiment.
Figure 2:
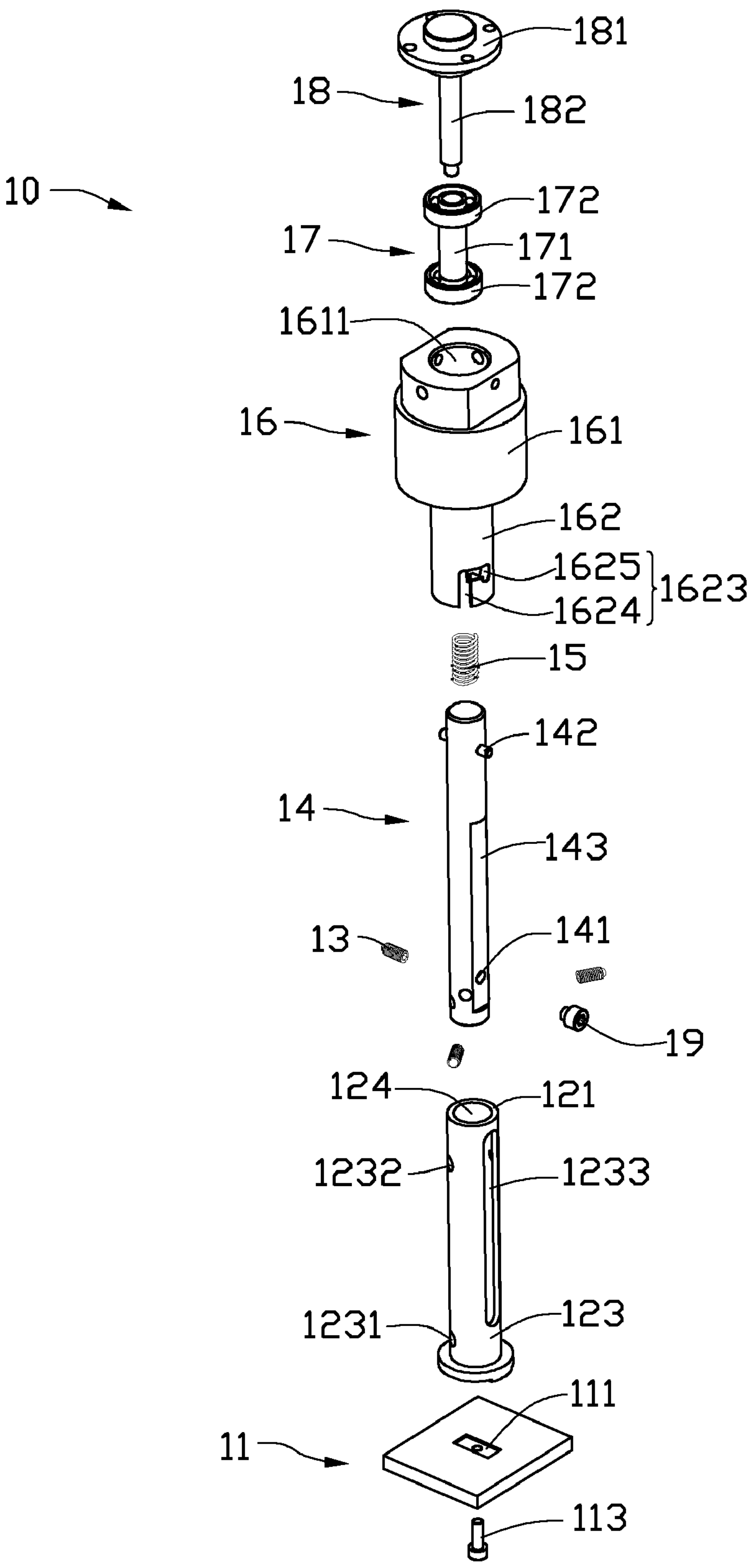
FIG. 2 is similar to FIG. 2, but viewed from another aspect.

FIGS. 1 and 2 show an exemplary adjustable fixture 10. The adjustable fixture 10 includes a clamping board 11, a telescopic sleeve 12, three latching assemblies 13, a telescopic shaft 14, a first elastic member 15, a base 16, a bearing 17, and a fastening seat 18. The clamping board 11 is fixed to one end of the telescopic sleeve 12. The telescopic sleeve 12 slidably receives the telescopic shaft 14 therein. The latching assemblies 13 are mounted on the telescopic sleeve 14, and are used to resist the telescopic sleeve 12. The telescopic shaft 14 is fastened to the base 16. The base 16 is rotatably mounted on the fastening seat 18 by the bearing 17.

The clamping board 11 includes a fastening hole 111 defined near a center thereof. The fastening hole 111 cooperates with a fastening pole 113 to fix the clamping board 11 to the telescopic sleeve 12. The clamping board 11 includes two clamping slots 112 respectively defined at two sides of the fastening hole 111, and is used to clamp workpieces (not shown) thereon.

The telescopic sleeve 12 includes an opened end 121, a closed end 122, and a peripheral wall 123 connecting the opened end 121 and the closed end 122. The closed end 122 and the peripheral wall 123 enclose a space cavity 124. The closed end 122 defines a connecting hole 1221 corresponding to the fastening hole 111. The peripheral wall 123 includes three upper through holes 1231 and three lower through holes 1232. The three upper through holes 1231 are defined adjacent to the closed end 122, and are equally disposed along the peripheral direction. The three lower through holes 1232 are defined adjacent to the opened end 121, and are equally disposed along the peripheral direction. One upper through hole 1231 corresponds to one lower through hole 1232. An interior surface of the peripheral wall 123 defines a groove 1234 (show in FIG. 5) corresponding to each upper through hole 1231 or lower through hole 1232. The peripheral wall 123 further defines a sliding slot 1233 extending axially. The upper through holes 1231, the lower through holes 1232, and the sliding slot 1233 communicate with each other via the cavity 124. In this embodiment, the sliding slot 1233 coincides with one upper through hole 1231 and one corresponding lower through hole 1232. The sliding slot 1233, the upper through holes 1231, and the lower through holes 1232 can be staggered relative to each other.

Figure 3:
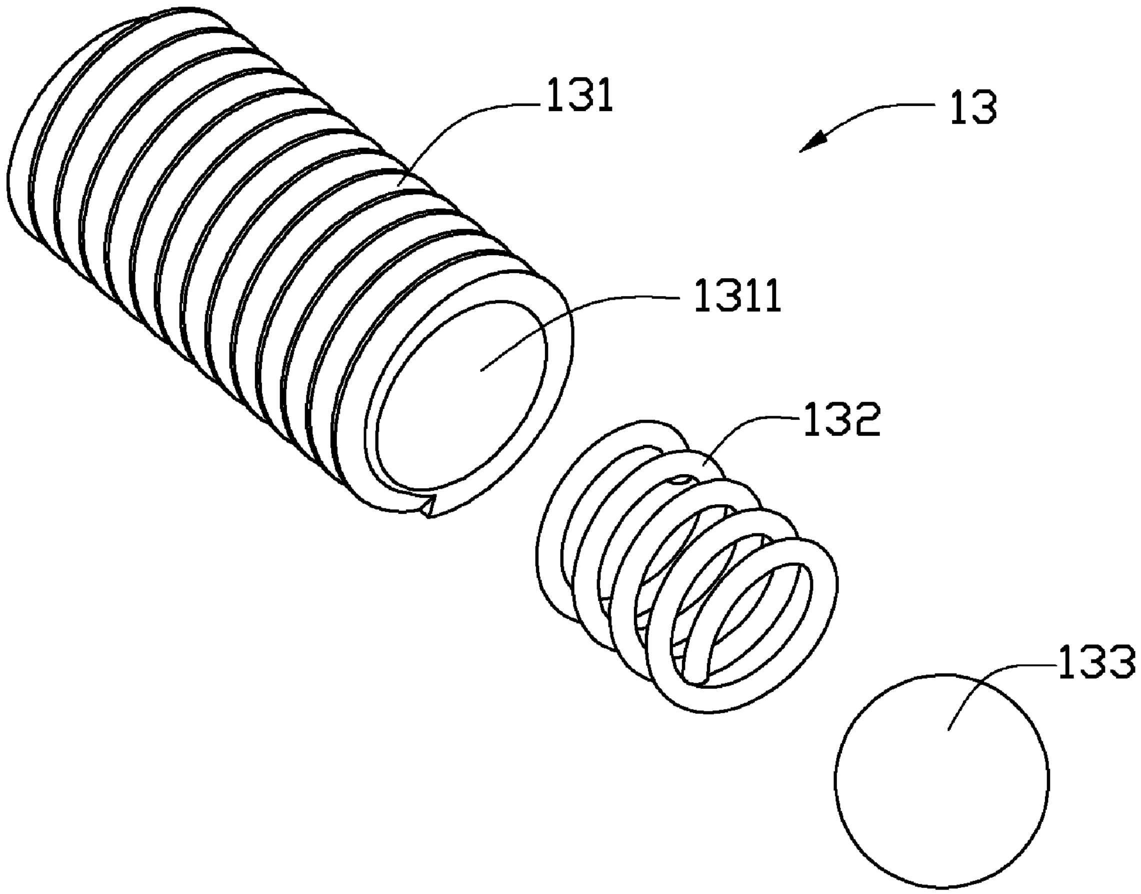
FIG. 3 is an isometric, exploded view of a latching assembly shown in FIG. 1.

Referring to FIG. 3, the latching assembly 13 includes an externally threaded receiving sleeve 131, a second elastic member 132, and a sphere 133. The receiving sleeve 131 defines a blind hole 1311 with a bottom wall (not shown). The blind hole 1311 receives the second elastic member 132 and the sphere 133 therein, and the second elastic member 132 is placed between the bottom wall and the sphere 133 under a predetermined tension.

The telescopic shaft 14 includes three screw holes 141 corresponding to the three upper through holes 1231 or the three lower through holes 1232 defined at one end thereof. Each screw hole 141 is defined through the telescopic shaft 14, and screws with the external threads of the receiving sleeve 131 to mount a latching assembly 13 therein. One screw hole 141 is used to fasten a sliding pole 19 therein. The sliding pole 19 includes a head portion 191 and an externally threaded tail portion 192. The tail portion 192 can be screwed into the screw hole 141. The telescopic shaft 14 further includes two latching poles 142 protruding from a peripheral wall thereof adjacent to the other end used to latch the shaft 14 to the base 16. The telescopic shaft 14 is cut partially to form a resisting surface 143, one of the screw holes 141 is on the resisting surface 143.

The first elastic member 15 is a compression spring received in the base 16. One end of the elastic member 15 resists the telescopic shaft 14, the other end resists the base 16.

The base 16 includes a main portion 161 and a connecting portion 162 protruding from the main portion 161. The main portion 161 is generally a column, and defines a receiving space 1611. The receiving space 1611 is configured for tightly receiving the bearing 17 therein. The connecting portion 162 is a hollow pole, and includes an opened 1622. A peripheral wall of the connecting portion 162 defines two symmetric "L"-shaped slots 1623 adjacent to the opened 1622. Each "L"-shaped slot 1623 includes a first slot section 1624 and a second slot section 1625 communicating with the first slot section 1624. The first slot section 1624 extends axially, and the second slot section 1625 extends circumferentially.

The bearing 17 includes a pole 171 and two bearing mechanisms 172 <wheel carries too much baggage, go broader> rotatably mounted to both ends of the pole 171. The pole 171 is a hollow pole used to partially receive the fastening seat 18 therein, and is fastened to the fastening seat 18. The bearing mechanisms 172 are received in the receiving space 1611 and fastened to the base 16.

The fastening seat 18 includes a fastening portion 181 and a pivoting portion 182 protruding from the fastening portion 181. The fastening portion 181 is mounted to a workplate (not shown). The pivoting portion 182 is inserted into the pole 171, and fastened with the pole 171.

Figure 4:
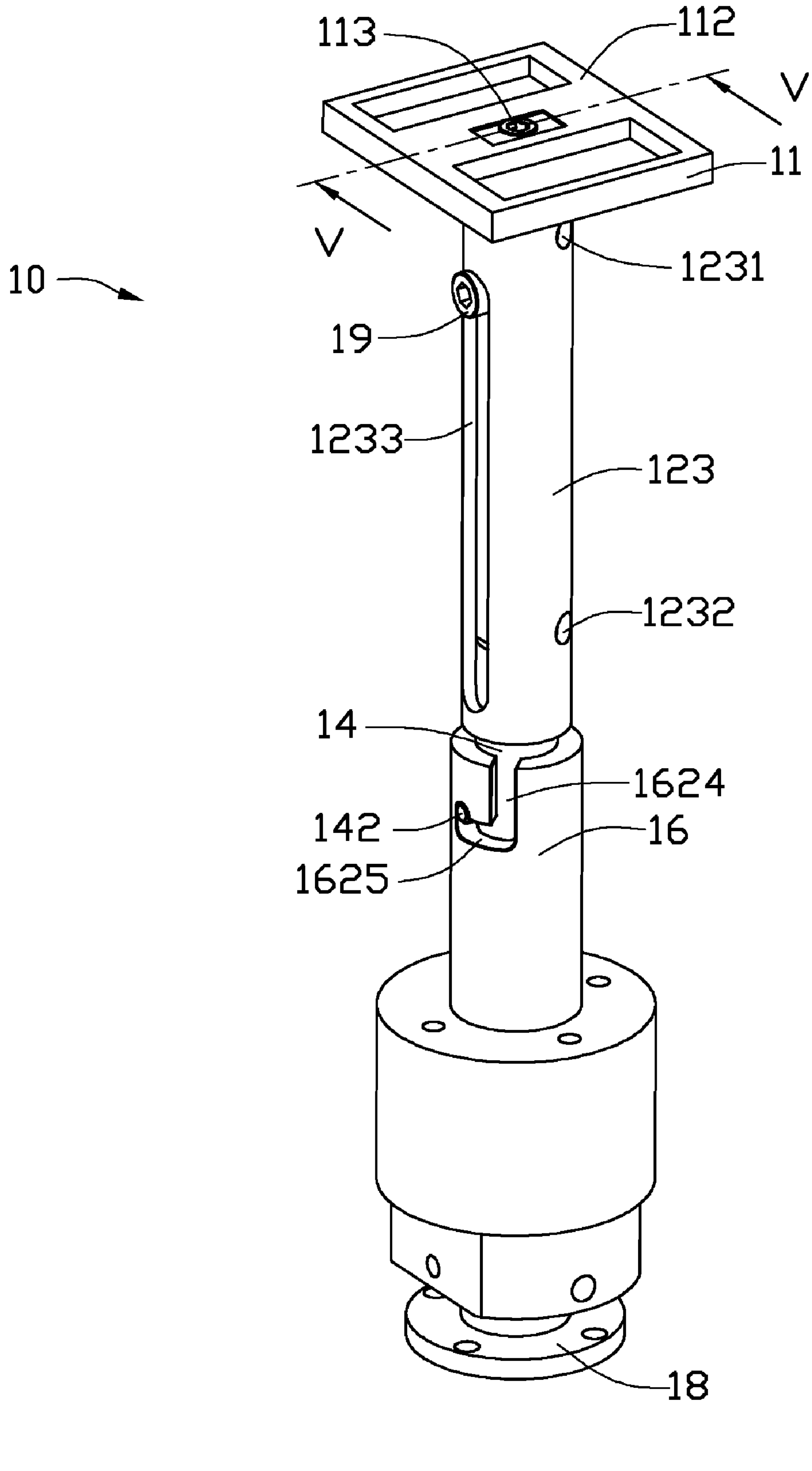
FIG. 4 is an assembled view of the adjustable fixture shown in FIG. 1.
Figure 5:
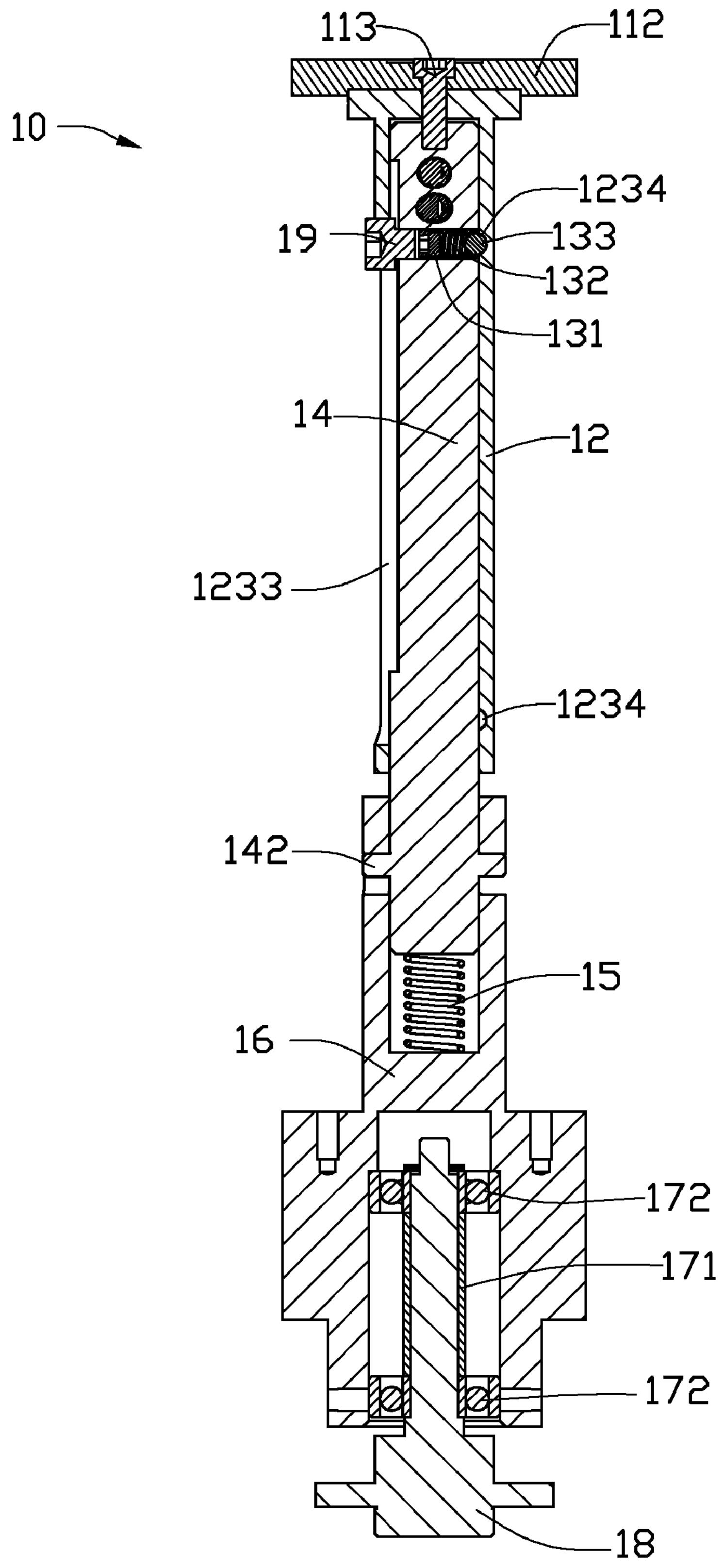
FIG. 5 is a cross-sectional view of the adjustable fixture taken along line V-V in FIG. 4.
Figure 6:
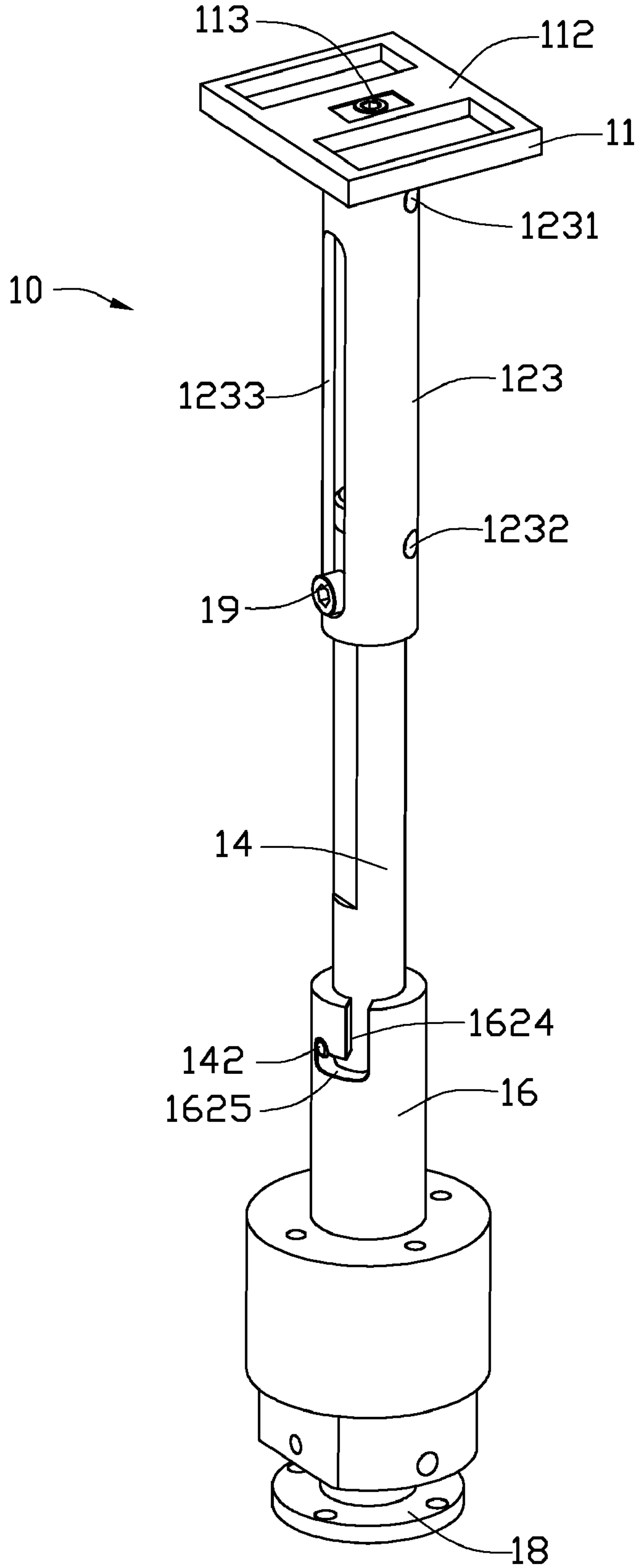
FIG. 6 is a schematic view showing the use of the adjustable fixture shown in FIG. 4.

Referring to FIGS. 4 and 5, in assembly, the telescopic shaft 14 is inserted into the cavity 124 of the telescopic sleeve 12, with the latching pole 142 adjacent to the opened end 121. Then the telescopic shaft 14 is pushed towards the closed end 122, while being rotated until the three screw holes 141 are aligned with the three upper through holes 1231, and the resisting surface 143 is aligned with the sliding slot 1233. The latching assemblies 13 are respectively screwed into the screw holes 141 through the through holes 1231, with the three spheres 133 facing the grooves 1234. The latching assemblies 13 are continued to be screwed into the screw holes 141 until the receiving sleeves 131 are completely received in the telescopic shaft 14. At this time, the spheres 133 are partially received in the grooves 1234 under the second elastic member 132. The tail portion 192 of the sliding pole 19 is screwed in the screw hole 141 on the resisting surface 143 until the head portion 191 of the sliding pole 19 is slidably received in the sliding slot 1233. The elastic member 15 is received in the connecting portion 162. The latching pole 142 is inserted into the first slot section 1624 and then into the second slot section 1625, thus mounting the telescopic shaft 14 to the base 16. The base 16 is rotatably mounted in the fastening seat 18 via the bearing 17. Thus, the adjustable fixture 10 is assembled.

In use, the adjustable fixture 10 can be adjusted via the sliding operation between the telescopic shaft 14 and the telescopic sleeve 12. The telescopic shaft 14 can be stably kept at the three upper through holes 1231 and the three lower through holes 1232, with the spheres 133 positioned in the grooves 1234. The adjustable fixture 10 allows rotation of the mounting board 11 relative to the fastening seat 18. Thus, the adjustable fixture can be adjusted in three dimensions.

It is to be understood, however, that even through numerous characteristics and advantages of the present disclosure have been set forth in the foregoing description, together with details of the structure and function of the disclosure, the disclosure is illustrative only, and changes may be made in detail, especially in matters of shape, size, and arrangement of sections within the principles of the disclosure to the full extent indicated by the broad general meaning of the terms, in which the appended claims are expressed.

What is claimed is:

1. An adjustable fixture comprising:

a clamping board used to mount a workpiece thereon;

a hollow telescopic sleeve, the clamping board being fastened to the telescopic sleeve;

a latching assembly;

a telescopic shaft, the telescopic sleeve slidably receiving the telescopic shaft therein, the latching assembly positioning the telescopic shaft relative to the telescopic sleeve; and a fastening seat, the telescopic shaft being rotatably mounted on the fastening seat;

wherein the latching assembly includes a receiving sleeve, an elastic member, and a sphere, the receiving sleeve defines a blind hole with a bottom wall, the blind hole receives the second elastic member and the sphere therein, and the second elastic member is placed between the bottom wall and the sphere, and has a predetermined pressure, and the receiving sleeve is fastened to the telescopic shaft, the sphere resists in the groove.

2. The adjustable fixture as claimed in claim 1, wherein the telescopic sleeve includes an opened end, a closed end, and a peripheral wall connecting the opened end and the closed end, the clamping board is mounted to the closed end, the telescopic shaft slidably received in the telescopic sleeve through the opened end, the peripheral wall defines a groove adjacent to the opened end and the closed end, the latching assembly resists in the groove.

3. The adjustable fixture as claimed in claim 2, wherein the peripheral wall further defines a through hole corresponding to the groove, the latching assembly is mounted on the telescopic shaft through the through holes.

4. The adjustable fixture as claimed in claim 1, further comprising a base, wherein the telescopic shaft is fastened to the base, the base is rotatably fastened to the fastening seat.

5. The adjustable fixture as claimed in claim 1, further comprising a bearing and a base, wherein the bearing includes a pole and two bearing mechanisms rotatably fastened to both ends of the pole, the pole is fastened to the fastening seat, the two bearing mechanisms are fastened to the base.

6. The adjustable fixture as claimed in claim 5, wherein the pole is a hollow pole, used to partially receive the fastening seat therein, the base defines a receiving space at one end thereof, the bearing mechanisms are received in the receiving space.

7. The adjustable fixture as claimed in claim 6, wherein the base further defines an "L"-shaped slot at the other end, the telescopic shaft includes a latching pole protruding from one end thereof, the latching pole latches in the "L"-shaped slot.

8. The adjustable fixture as claimed in claim 7, wherein the "L"-shaped slot includes a first slot section and a second slot section communicating with the first slot section, the first slot section extends axially, the second slot section extends circumferentially.

9. The adjustable fixture as claimed in claim 1, wherein the telescopic sleeve defines a sliding slot extending axially, the telescopic shaft includes a sliding pole protruding therefrom, the sliding pole are slidably received in the sliding slot.

10. An adjustable fixture comprising:

a clamping board used to mount a workpiece thereon;

a hollow telescopic sleeve, the clamping board being fastened to the telescopic sleeve;

a latching assembly;

a telescopic shaft, the telescopic sleeve slidably receiving the telescopic shaft therein, the latching assembly positioning the telescopic shaft relative to the telescopic sleeve;

a base; and a bearing;

wherein the telescopic shaft is fastened to the base, the bearing includes a pole and two bearing mechanisms rotatably fastened to both ends of the pole, and the two bearing mechanisms are fastened to the base.

11. The adjustable fixture as claimed in claim 10, wherein the telescopic sleeve includes an opened end, a closed end, and a peripheral wall connecting the opened end and the closed end, the clamping board is mounted to the closed end, the peripheral wall defines a groove adjacent to the opened end and the closed end, the latching assembly resists in the groove.

12. The adjustable fixture as claimed in claim 11, wherein the peripheral wall further defines a through hole corresponding to the groove, the latching assembly is mounted on the telescopic shaft through the through holes.

13. The adjustable fixture as claimed in claim 10, wherein the latching assembly includes a receiving sleeve, an elastic member, and a sphere, the receiving sleeve defines a blind hole with a bottom wall, the blind hole receives the second elastic member and the sphere therein, and the second elastic member is placed between the bottom wall and the sphere, and has a predetermined pressure, and the receiving sleeve is fastened to the telescopic shaft, the sphere resists in the groove.

14. The adjustable fixture as claimed in claim 10, wherein the base defines a receiving space at one end thereof, and the bearing mechanisms are received in the receiving space.

15. The adjustable fixture as claimed in claim 14, wherein the base further defines an “L”-shaped slot at the other end, the telescopic shaft includes a latching pole protruding from one end thereof, the latching pole latches in the “L”-shaped slot.

16. The adjustable fixture as claimed in claim 15, wherein the “L”-shaped slot includes a first slot section and a second slot section communicating with the first slot section, the first slot section extends axially, the second slot section extends circumferentially.

17. The adjustable fixture as claimed in claim 10, wherein the telescopic sleeve defines a sliding slot extending axially, the telescopic shaft includes a sliding pole protruding therefrom, and the sliding pole are slidably received in the sliding slot.

18. An adjustable fixture comprising:

a clamping board used to mount a workpiece thereon;

a hollow telescopic sleeve including an opened end and a closed end, the clamping board being fixed to the closed end;

a telescopic shaft, one end of the telescopic shaft partially and slidably received in the telescopic sleeve through the opened end, another end of the telescopic shaft exposed from the opened end;

a latching assembly positioning the telescopic shaft relative to the telescopic sleeve;

a fastening seat, the telescopic shaft exposed from the opened end being rotatably mounted on the fastening seat.

19. The adjustable fixture as claimed in claim 18, further comprising a base and a bearing, wherein the telescopic shaft is fastened to the base, the base is rotatably mounted in the fastening seat via the bearing.

* * * * *